United States Patent [19]

Berrer et al.

[11] 4,242,119

[45] Dec. 30, 1980

[54] AGENT FOR COMBATING SEA-WATER ALGAE

[75] Inventors: Dagmar Berrer, Riehen, Switzerland; Joachim Lorenz, Bensheim; Reinhardt Grade, Zwingenberg-Rodau, both of Fed. Rep. of Germany

[73] Assignee: Ciba-Geigy Corporation, Ardsley, N.Y.

[21] Appl. No.: 7,138

[22] Filed: Jan. 29, 1979

[30] Foreign Application Priority Data

Feb. 3, 1978 [CH] Switzerland .................... 1212/78

[51] Int. Cl.³ .................... A01N 43/70; C09D 5/14
[52] U.S. Cl. .................... 71/67; 71/93; 106/18.33
[58] Field of Search .................... 71/67, 93; 106/18.33

[56] References Cited

U.S. PATENT DOCUMENTS

| 3,629,256 | 12/1971 | Berrer et al. | 71/93 |
| 3,629,257 | 12/1971 | Berrer et al. | 260/249.8 |
| 3,741,745 | 6/1973 | Berrer et al. | 71/93 |
| 3,759,690 | 9/1973 | Berrer et al. | 71/93 |
| 3,799,925 | 3/1974 | Nikles | 71/93 X |
| 3,873,298 | 3/1975 | Bieringer et al. | 71/87 |
| 4,012,503 | 3/1977 | Freiman | 71/67 X |

FOREIGN PATENT DOCUMENTS

49-061336 6/1974 Japan.
52-021331 2/1977 Japan.
1473298 5/1977 United Kingdom.

*Primary Examiner*—Catherine L. Mills
*Attorney, Agent, or Firm*—Luther A. R. Hall

[57] ABSTRACT

A sea-water algicidal composition containing a triazine of the group comprising 2-methylthio-4-cyclopropylamino-6-($\alpha,\beta$-dimethylpropylamino)-s-triazine (I); 2-methylthio-4-cyclopropylamino-6-t-butylamino-s-triazine (II); and 2-methylthio-4-ethylamino-6-($\alpha,\beta$-dimethylpropylamino)-s-triazine.

5 Claims, No Drawings

AGENT FOR COMBATING SEA-WATER ALGAE

The present invention relates to the use of triazines as sea-water algicides, to the compositions containing these sea-water algicides, and to 2-methylthio-4-cyclopropylamino-6-($\alpha,\beta$-dimethylpropylamino)-s-triazine and to its use as an algicide.

The use of 2-alkylthio-4,6-diamino-s-triazines as selective agents for combating weeds and wild grasses is known for example from the German Offenlegungsschrift No. 1,914,014. And in recent times the high effectiveness of such triazines against fresh-water algae has also been recognised. Thus, for example, their use as algicides against fresh-water algae, such as Spirogyra, Hydrodictyon and Oedogeniales, has been described in the Japanese Offenlegungsschrift No. 49,061-336. It is reported in Japanese Offenlegungsschrift No. 52,021-331 and in the U.S. Pat. Spec. No. 4,012,503 that related triazines display a certain activity also against sea-water algae. Although the minimum inhibiting concentrations (MIC) are low, the triazines mentioned are insufficiently effective against sea-water algae because the full level of activity of these triazines is attained only after a long period of action. Algae require a specific length of time in still water in order to become firmly fixed to the surfaces to be protected, such as ships' hulls, and so forth. It has been shown that a length of time of 2 to 4 hours suffices for sea-water algae to adhere firmly enough not to be washed away by turbulence. The requirement that a sea-water algicide has therefore to satisfy is that it attains a high level of effectiveness very rapidly.

There has now been found a small group of triazines which, compared with the known triazine algicides, surprisingly attain their full effectiveness with comparable MIC values more quickly, a factor which renders them of great practical importance.

The present invention relates therefore to the use of 2-methylthio-4-cyclopropylamino-6-($\alpha,\beta$-dimethylpropylamino)-s-triazine (I), 2-methylthio-4-cyclopropylamino-6-t-butylamino-s-triazine (II) and 2-methylthio-4-ethylamino-6-($\alpha,\beta$-dimethylpropylamino)-s-triazine (III) as algicides for combating sea-water algae. The triazines (II) and (III) as herbicides are known compounds: triazine (I) is a novel compound.

The compounds to be used according to the invention are produced in a known manner, the production thereof being described in German Offenlegungsschrift No. 1,914,014.

Cyanuric chloride can be reacted with an amine, selected from the group comprising cyclopropylamine, t-butylamine, ethylamine or $\alpha,\beta$-dimethylpropylamine; and the dichloroamino-s-triazine obtained as intermediate converted with methyl mercaptan or with a salt thereof into a methylthio-chloroamino-s-triazine derivative, which is then reacted with an amine not used in the first step, in order to introduce the second amine substituent mentioned in the formulae I, II and III. It is also possible to change the sequence of the 2nd and 3rd steps of the reaction course described above. The methylthio groups in this case are introduced, as described in the German Offenlegungsschrift No. 1,914,014, by means of thiourea and dimethyl sulfate in the presence of basic substances. Preferably, an acid-binding agent, such as a tertiary amine, an alkali metal hydroxide or alkali metal alcoholate, is used in all the reaction steps, and the reactions are performed in an inert organic solvent. The use of ketones, such as acetone or methyl ethyl ketone, is particularly suitable for this purpose.

The compounds according to the invention are used in all cases where objects, which are to be protected against the growth of algae, are exposed to sea water. The objects concerned are in particular: hulls of ships, structures in water, buoys, fishing nets, and also cooling systems and pipe systems through which sea water flows. The triazines in general protect all materials which come into contact with sea water from becoming overgrown with algae, for example materials such as wood, cellulose, textiles and leather, paints, lacquers, for example antifouling paints and similar coating materials, optical glass and other types of glass, plastics, rubber and adhesives, and also other materials.

Depending on the purpose of application, the compounds are used in the concentration ranges known to the expert. The limits of the customary concentrations are indicated by the following values: whereas in cooling water it suffices to have concentrations in the ppm range, concentrations up to 40 percent by weight are customary in antifouling recipes.

The compounds can be applied, in the pure form or together with carriers, as dusts, scattering or spraying agents. They may also be dissolved or suspended in liquid media, and, where it is desired to form homogeneous dispersions, wetting agents or emulsifying agents can be used to promote the uniform dispersion of the active ingredient. And preferably further biocides are added.

A particularly preferred field of application is that of protective coating agents, especially antifouling paints, which contain 0.5–40 percent by weight, preferably 3 to 15 percent by weight, relative to the total mixture, of a compound of the formula I, II or III, together with the customary base materials and additives.

Customary base materials for antifouling paints are the lacquer raw materials which are designated as binders and which are known to the expert, such as natural and synthetic resins, homo- and copolymeric products with the monomers vinyl chloride, vinylidene chloride, styrene, vinyl toluene, vinyl esters, acrylic acid and methacrylic acid, as well as esters thereof, and also chlorinated rubber, natural and synthetic rubber, optionally chlorinated or cyclised, also reaction resins such as epoxide resins, polyurethane resins, or unsaturated polyesters which can optionally be converted, by the addition of curing agents, into film-forming higher molecular products.

The binders can be liquid or they can be present in the dissolved form. In the case of dissolved binders, also thermoplasts, a protective film can be formed by evaporating off the solvent. Solid coating agents can be applied for example in the powder coating process to the objects to be protected. Further customary base materials are for example tar, modifiers, dyes, inorganic or organic pigments, fillers and curing agents.

Finally, the compounds according to the invention can also be used in elastomeric coatings, or can be incorporated into plastics.

In practice, substances having an algicidal action are frequently used with other biocides. An advantageous combination in the present case is the combination with a biocide which acts against animal growth organisms. Suitable biocides are for example $Cu_2O$, zinc oxide or triorganotin compounds, such as tributyl tin oxide, tributyl tin fluoride or triphenyl tin chloride, or in general such substances which are known to the expert as being effective against animal growth organisms. Also the combination with further algicides is in many cases of advantage.

The invention therefore relates also to compositions containing a triazine I, II or III. They are preferably protective coating compositions and especially antifouling paints containing in each case a triazine I, II or III.

The triazines I, II and III are effective algicides for combating species of algae occurring in sea water. The Enteromorpha may be mentioned here as being the most important and most common species.

The present invention also relates to the triazine I, 2-methylthio-4-cyclopropylamino-6-($\alpha,\beta$-dimethylpropylamino)-s-triazine, which is a novel compound. The compound has, in addition to the stated good properties for combating sea-water algae, also the property of being effective against fresh-water algae, which renders possible its application in various water systems, such as cooling-water plants or swimming baths. Furthermore, this triazine is suitable as a herbicide.

The following Examples further illustrate the invention.

EXAMPLE 1

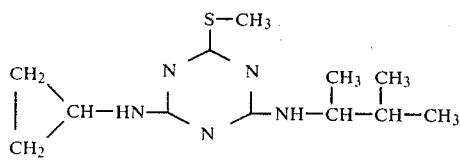

15.1 g of 2-methylthio-4-cyclopropylamino-6-chloro-s-triazine is dissolved in 150 ml of toluene, and at room temperature 6.1 g of $\alpha,\beta$-dimethylpropylamine is added dropwise. After 1 hour's stirring, 9.2 g of 30.4% sodium hydroxide solution is added, and the mixture is heated at 45°–50° C. for 2 hours. The toluene is separated, and the residue is washed neutral and dried. The resulting 2-methylthio-4-cyclopropylamino-6-($\alpha,\beta$-dimethylpropylamino)-s-triazine is distilled (b.p. 146°–147° C./0.001 mm).

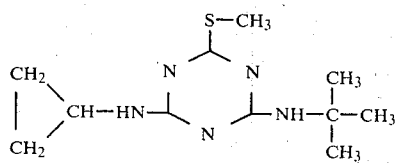

10.4 g of 2-methylthio-4-tert-butylamino-6-chloro-s-triazine is dissolved in 40 ml of toluene, and at 22°–32° C. 2.57 g of cyclopropylamine is added dropwise. After 1 hour's stirring, 5.92 g of 30% sodium hydroxide solution is added, and the mixture is heated at 35° C. for 2 hours. The toluene is separated, and the residue is washed neutral and dried. The resulting 2-methylthio-4-tert-butylamino-6-cyclopropylamino-s-triazine is recrystallised from methanol/water (m.p. 121°–123° C.).

EXAMPLE 3

2-Methylthio-4-ethylamino-6-($\alpha,\beta$-dimethylpropylamino)-s-triazine (b.p. 143°–145° C./0.001 mm) can be produced in an analogous manner.

EXAMPLE 4

The examination of the action against green alga, Enteromorpha, the most important genus with regard to sea-water fouling, is carried out in sterilely filtered sea water which contains an erdschreiber solution. This solution is composed of a nutrient extract, phosphate and nitrate. The incubation of Enteromorpha intestinalis takes place in a light thermostat at 18° C. with a 14-hour light—10-hour darkness cycle.

The algae cultured in this manner are exposed to the algicides to be examined, for a short period of time (2 or 4 hours), in sea water. The minimum killing concentration (MKC) is determined by taking the algae from the sea water, after a specific amount of algicide contained in the water has been acting for the set period of time, washing the algae and, after a 6–8 weeks' renewed incubation in fresh sea water, examining the algae with respect to the extent of growth or of destruction.

The minimum killing concentration (MKC) indicates the amount of substance necessary to damage the algae within a specific time to such a degree that it cannot recover in fresh sea water and consequently dies off.

The results of these tests after 4 hours are summarised in Table 1 and those after 2 hours in Table 2. The extraordinarily low MKC values of the triazines I, II and III verify the surprisingly rapid effectiveness of these compounds.

Table 1

| Algicide | MKC in ppm after 4 h |
| --- | --- |
| 2-methylthio-4-ethylamino-6-isopropylamine-triazine (according to U.S. Pat. specification No. 4,012,503) | 5 |
| 2-methylthio-4,6-diethylamino-s-triazine (according to Jap. Offenlegungsschrift No. 49, 061-336) | 5 |
| 2-methylthio-4,6-diisopropylamino-s-triazine (according to Jap. Offenlegungsschrift No. 52, 021-331) | >5 |
| 2-methylthio-4-cyclopropylamino-6-isopropylamino-s-triazine | >5 |
| 2-methylthio-4-cyclopropylamino-6-(1',3'-dimethylbutylamino)-s-triazine | 5 |
| 2-methylthio-4-cyclopropylamino-6-sec-butylamino-s-triazine | >5 |
| 2-methylthio-4-n-propylamino-6-t-butylamino-s-triazine | >5 |
| 2-methylthio-4-ethylamino-6-t-butylamino-s-triazine | 5 |
| 2-methylthio-4-cyclopropylamino-6-($\alpha,\beta$-dimethylpropylamino)-s-triazine (I) | 0.5–1 |
| 2-methylthio-4-cyclopropylamino-6-t-butylamino-s-triazine (II) | 0.5 |
| 2-methylthio-4-ethylamino-6-($\alpha,\beta$-dimethylpropylamino)-s-triazine (III) | 1 |

Table 2

| Algicide | MKC in ppm after 2 h |
| --- | --- |
| 2-methylthio-4-ethylamino-isopropylamino-s-triazine (according to U.S. Pat. Specification No. 4,012,503) | >7 |
| 2-methylthio-4,6-diethylamino-s-triazine (according to Jap. Offenlegungsschrift No. 49,061,336) | >7 |
| 2-methylthio-4-cyclopropylamino-6-(1',3'-dimethylbutylamino)-s-triazine | >7 |
| 2-methylthio-4-ethylamino-6-t-butylamio-s-triazine | >7 |
| 2-methylthio-4-cyclopropylamino-6-($\alpha,\beta$-dimethylpropylamino)-s-triazine (I) | 1–2 |
| 2-methylthio-4-cyclopropylamino-6-t-butylamino-s-triazine (II) | 1–2 |
| 2-methylthio-4-ethylamino-6-($\alpha,\beta$-dimethylpropylamino)-s-triazine (III) | 2–3 |

What is claimed is:
1. A method of combatting sea-water algae which consists essentially of adding an effective amount of a triazine selected from the group consisting of 2-methylthio-4-cyclopropylamino-6-(α,β-dimethylpropylamino)-s-triazine (I); 2-methylthio-4-cyclopropylamino-6-tert-butylamino-s-triazine (II); and 2-methylthio-4-ethylamino-6-(α,β-dimethylpropylamino)-s-triazine (III) to sea-water in a sea-water cooling system or to a composition or material to be exposed to sea-water.

2. A method according to claim 1 where the sea-water alga is Enteromorpha.

3. A method according to claim 1 for protecting a composition or material exposed to sea-water from becoming overgrown with sea-water algae.

4. A method according to claim 3 where the composition or material is a ship's hull, a buoy, a structure in sea-water or a fishing net.

5. A method according to claim 3 where the material is a sea-water cooling system.

* * * * *